United States Patent [19]
Cooper et al.

[11] Patent Number: 6,067,857
[45] Date of Patent: May 30, 2000

[54] BRAKING ELEMENT PROCESSING SYSTEM

[75] Inventors: Robert A. Cooper; Thomas P. Plunkett, both of Ann Arbor, Mich.

[73] Assignee: Balance Technology, Inc., Ann Arbor, Mich.

[21] Appl. No.: 09/031,262

[22] Filed: Feb. 26, 1998

Related U.S. Application Data

[60] Provisional application No. 60/033,809, Feb. 28, 1997.

[51] Int. Cl.[7] .............................. G01M 1/02; G01N 27/90
[52] U.S. Cl. .............................................. 73/462; 324/226
[58] Field of Search .................... 73/462, 460; 324/226, 324/240, 242

[56] References Cited

U.S. PATENT DOCUMENTS

| | | | |
|---|---|---|---|
| 3,232,118 | 2/1966 | Hack | 73/462 |
| 4,480,471 | 11/1984 | Kögler et al. | 73/462 |
| 4,481,471 | 11/1984 | Miller et al. | 324/240 |
| 5,189,912 | 3/1993 | Quinlan et al. | 73/462 |

*Primary Examiner*—John E. Chapman
*Attorney, Agent, or Firm*—Rohm & Monsanto, PLC

[57] ABSTRACT

A processing arrangement for a brake element for a vehicle employs a rotational support, such as a precision collet arrangement, for supporting the brake element rotatably about a fixed axis of rotation. The brake element and the spindle are rotated by a drive arrangement that causes the brake element to rotate about the axis of rotation while a rotary encoder that is coupled to the drive arrangement produces a rotation data signal containing rotational information responsive to the rotation of the brake element. Residual unbalances are measured by the production of an unbalance data signal that is responsive to forces that are themselves responsive to a residual unbalance of the brake element. In addition, a surface dimension detector produces a surface dimension data electrical signal that is responsive to a dimensional characteristic of a surface of the brake element. A surface defect detector that typically is in the form of an eddy current probe, produces a surface defect data electrical signal responsive to the presence of a predetermined surface defect of the brake element. The various data signals are correlated in a signal processor to produce rotationally a correlated signal responsive to the rotation data signal, the unbalance data electrical signal, the surface dimension data signal, and the surface defect data electrical signal. Data corresponding to the residual unbalance, the dimensions, and the surface condition of the brake element is presented on a computer monitor and can be stored for quality control purposes and for use in other automated systems, such unbalance correction equipment.

28 Claims, 2 Drawing Sheets

BRAKING ELEMENT PROCESSING SYSTEM

RELATIONSHIP TO OTHER APPLICATION

This application claims the benefit of the filing date of Provisional application for U.S. Pat. No. 60/033,809, filed on Feb. 28, 1997.

BACKGROUND OF THE INVENTION

1. Field of the Invention

This invention relates generally to inspection systems for manufactured components, and more particularly, to an integrated system for processing machined rotatory metal workpieces, such as braking elements for use in vehicles, the workpieces being processed and inspected from the standpoints of balance, dimensional gaging, and/or detection of surface flaws.

2. Description of the Related Art

Many machined workpieces, such as rotors and drums for the braking system of vehicles, are required to be inspected from a variety of standpoints. These include, for example, balance measurement, whereby the magnitude and location of residual unbalance of the workpiece is determined; dimensional gaging, to determine whether the workpiece is dimensioned within predetermined parameters; and surface inspection, for determining the location of surface flaws and cracks.

In the present art, the various inspections and measurements that are required before a critical rotatory workpiece, such as an automotive brake rotor, can be released for use, are performed at respective stations, employing respective machines. Such a processing system required a good deal of time in transferring the workpiece from station to station, significant investment in capital equipment for the various machines, and notwithstanding such expense, will not yield data that is correlated to an angular index point of the workpiece for all such measurements and inspections. Accordingly, there is need for a need for a simple, cost-effective, inspection and processing system for a critical rotatory workpiece wherein all measurement information is correlated to a common index point on the workpiece.

SUMMARY OF THE INVENTION

The present invention involves the incorporation of dimensional gaging capability into a dynamic balance station. In a further embodiment of the invention, surface flaw and crack detection capability is incorporated into the dynamic balance station. Not only does the incorporation of such additional capability into the dynamic balance station eliminate a complete stand-alone machine or station in an automatic processing system, it also takes advantage of the fact that in the dynamic balance station there is already present precision tooling for holding the workpiece, which is installed on a precision spindle coupled to a stable drive arrangement. The present arrangement therefore produces several types of data that are correlated, whereby certain deficiencies in the process of manufacturing the rotatory workpiece can readily be ascertained.

In accordance with the invention, a processing system for rotatory element, such as a brake rotor, is provided with a support arrangement for supporting the rotatory element rotatably about a fixed axis of rotation. Rotation is effected by a rotary drive system while a rotary encoder that is coupled to the drive system produces a rotation data signal containing rotational information responsive to the rotation of the rotatory element. An unbalance measuring system produces an unbalance data signal responsive to forces responsive to a residual unbalance characteristic of the rotatory element. Simultaneously, a surface detector produces a surface data electrical signal responsive to a predetermined characteristic of the surface of the rotatory element and a first signal correlator produces a correlated signal responsive to the rotation data signal and the unbalance data electrical signal. The signal correlator has an input for receiving the unbalance data electrical signal and a further input for receiving the rotation data signal. A signal processor processes the surface data electrical signal and the correlated unbalance data signal.

In one embodiment of the invention, there is provided a further signal correlator that produces a further correlated data signal responsive to the unbalance data electrical signal, the rotation data signal, and the surface data signal. An indicator, such as a computer monitor, produces an indication responsive to the further correlated data signal. In another embodiment, the rotatory element is of the type having at least a first surface that is desired to be measured dimensionally, and the surface detector includes a first gaging probe that produces the surface data electrical signal containing data responsive to a dimensional characteristic of the first surface of the rotatory element. In this embodiment, there is farther provided a second gaging probe that produces a further surface data electrical signal containing data responsive to a dimensional characteristic of a second surface of the rotatory element. A multi-channel amplifier receives the surface data electrical signal and the further surface data electrical signal, and provides at an output thereof a dimensional data signal that is responsive to the dimensional characteristics of the first and second surfaces of the rotatory element.

In a specific illustrative embodiment of the invention, there is provided a gaging probe carrier for displacing the second gaging probe from a first position in the vicinity of the second surface of the rotatory element to a second position distal from the rotatory element. Such displacement greatly facilitates the installation of the workpiece onto the rotary support. The gaging probe carrier includes an arrangement for establishing the first position of the second gaging probe to be in predetermined fixed relation to the first gaging probe. In a further embodiment, the gaging probe carrier further includes a gaging probe drive system for driving the second gaging probe from the first position to the second position.

In a still further embodiment, the surface detector includes a surface defect detector that produces a surface defect data signal responsive to a predetermined surface defect of the rotatory element. In a practicable embodiment of the invention, the surface defect detector includes an eddy current probe. There is additionally provided a detector carrier for displacing the surface defect detector from a first position in the vicinity of the rotatory element to a second position distal from the rotatory element, in part for facilitating installation of the rotatory element. A surface defect detection drive system is used to drive the surface defect detector between the first and second positions. Such a surface defect detection drive system includes first and second drive arrangements for driving the surface defect detector along respective axes of motion. The first and second drive arrangements include a servo motor drive arrangement and an air driven slide arrangement, respectively.

In one embodiment of the invention, the unbalance measuring arrangement system is hard mounted.

In accordance with a further apparatus aspect of the invention, a processing arrangement for a brake element for a vehicle is provided with a support arrangement for supporting the brake element rotatably about a fixed axis of rotation, while a drive system drives the brake element to rotate about the axis of rotation. A rotary encoder is coupled to the drive system and has an output that produces a rotation data signal that contains rotational information responsive to the rotation of the brake element. An unbalance measuring system produces an unbalance data signal responsive to forces responsive to a residual unbalance characteristic of the brake element, and a surface dimension detector produces a surface dimension data electrical signal responsive to a predetermined dimensional characteristic of the surface of the brake element. A surface defect detector produces a surface defect data electrical signal responsive to the presence of a predetermined surface defect of the brake element. Additionally, a signal correlator produces a correlated signal responsive to the rotation data signal, the unbalance data electrical signal, the surface dimension data signal, and the surface defect data electrical signal. A signal processor processes the correlated signal.

In a highly advantageous embodiment of the invention, the support arrangement includes a precision spindle that is arranged to support the brake element in a fixed axial position while it is rotatable about the fixed axis of rotation. There is additionally provided a fixed support, and the unbalance measuring system, in this specific illustrative embodiment of the invention, includes a force measuring block that is interposed between the precision spindle and the fixed support.

In a specific illustrative embodiment of the invention, the surface dimension detector includes a first linear voltage differential transformer probe that is arranged to communicate with a first surface of the brake element. Additionally, the surface dimension detector includes a second linear voltage differential transformer probe that is arranged to communicate with a second surface of the brake element, and a dimension detector carrier displaces the second linear voltage differential transformer probe from a first position in the vicinity of the second surface of the brake element to a second position distal from the brake element.

The surface defect detector, in this specific embodiment, includes an eddy current detector probe. In a further embodiment, the signal processor includes data acquisition circuitry that acquires data contained in respective ones of the rotation data signal, the unbalance data electrical signal, the surface dimension data signal, and the surface defect data electrical signal. A central processor unit produces an output data signal that is responsive to the rotation data signal, the unbalance data electrical signal, the surface dimension data signal, and the surface defect data electrical signal. A data bus couples the data acquisition circuitry to the central processor unit. Additionally in this embodiment there are provided a display that is coupled to the central processor unit and produces a visual indication responsive to the rotation data signal and the unbalance data electrical signal, and a data storage system that stores data responsive to the rotation data signal and the unbalance data electrical signal.

In accordance with a method aspect of the invention, there is provided a method of processing a rotary element. The method includes the steps of:

installing the rotary element on a rotatable spindle;
rotating the rotary element and the rotatable spindle;
producing a rotation signal responsive to the rotation of the rotary element in the step of rotating;

producing an unbalance signal responsive to the rotation of the rotatory element in the step of rotating; and
producing a dimension signal responsive a dimensional characteristic of the rotatory element during the step of rotating.

In one embodiment of this method aspect of the invention, there is provided the further step of acquiring data responsive to the rotation signal, the unbalance signal, and the dimension signal. Additionally, there is provided the step of producing a visual indication responsive to the data obtained in the step of acquiring data.

In a still further embodiment, prior to performing the step of producing a dimension signal, there is performed the step of translating a dimensional probe to a predetermined location with respect to the rotatory element. A surface defect signal that is responsive a surface characteristic of the rotatory element is also produced during the step of rotating.

In a specific illustrative embodiment of the invention, prior to performing the step of producing a surface defect signal there is provided the further step of translating an eddy current probe to a predetermined location with respect to the rotatory element. The eddy current probe is further translated across a surface of the rotatory element, in some embodiments of the invention.

BRIEF DESCRIPTION OF THE DRAWING

Comprehension of the invention is facilitated by reading the following detailed description, in conjunction with the annexed drawing, in which.

DETAILED DESCRIPTION

Figure 1:
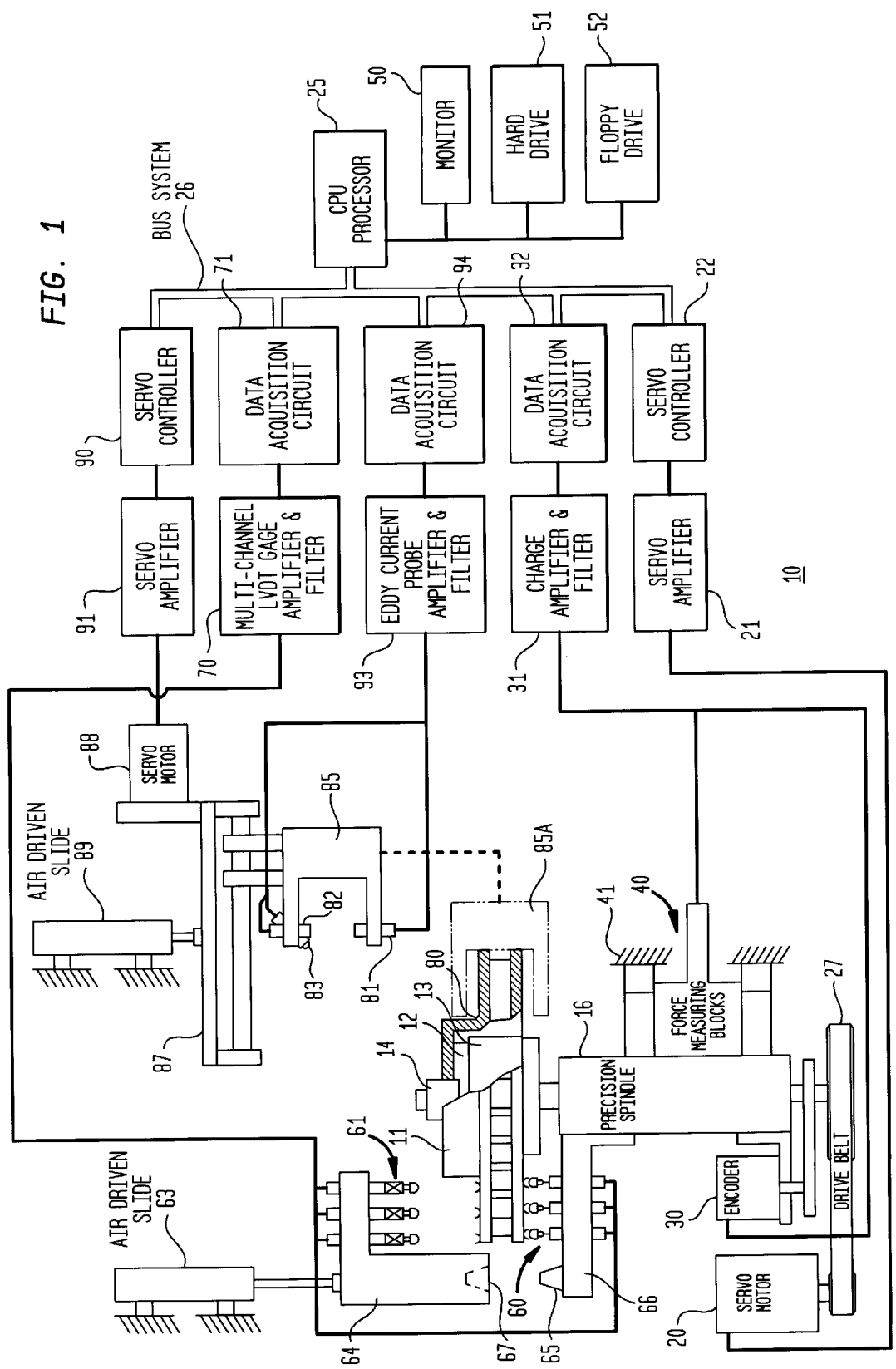
FIG. 1 is a partially schematic, partially cross-sectional, and partially function block representation of a specific illustrative embodiment of the invention wherein the workpiece is configured as an automotive brake rotor, the embodiment being characterized with the capabilities of measuring residual unbalance, detecting surface flaws, and measuring dimensional variations.

FIG. 1 is a schematic, cross-sectional, and function block representation of a workpiece processing system 10 that advantageously will, in accordance with the invention, generate and store data corresponding to dimensional gaging measurements, the presence of surface flaws, and residual unbalance, of a workpiece 11. In this illustrative embodiment of the invention, workpiece 11 is configured as an automotive brake rotor. Workpiece 11 is shown in FIG. 1 to be installed in a rest ring 12 which is disposed on a collet actuator 13. A precision collet 14 ensures that the workpiece remains secured to a precision spindle 16. The precision spindle is rotated in response to a torque applied by a servo motor 20 that rotates in response to signals received from a servo amplifier 21. The servo amplifier is responsive to a servo controller 22 that receives signals from a CPU processor 25 via a bus system 26. In this specific embodiment, torque from the servo motor is transmitted to the precision spindle via a drive belt arrangement 27. Information corresponding to the instantaneous angular position of precision spindle 16 is generated by an encoder 30 that conducts the signal to a charge amplifier and filter 31. Corresponding data is acquired in data acquisition circuit 32 and is then provided to processor 25 via bus system 26.

A force measuring system 40, which may include a plurality of force measuring blocks configured as piezoelectric detectors (not specifically shown in this figure) are arranged between precision spindle 16 and a housing generally designated as 41. The housing functions as a firm mechanical ground that will not itself move or vibrate irrespective of the forces applied thereto. Thus, as workpiece 11 is rotated, the residual unbalance in the workpiece results in a vibration or force having a period that corresponds to the frequency of rotation of the workpiece. The unbalance force is transmitted laterally from precision spindle 16 to the force measuring system 40. Since the force measuring system is fixed at one end at housing 41, a corresponding vibratory force (compression and tensile) is exerted on the force measuring system and a corresponding signal is conducted to charge amplifier and filter 31. The force signal is correlated to the angular position of the precision spindle by operation of encoder 30, and therefore data acquisition circuit 32 contains information relating to the force resulting from the residual unbalance of the rotated work-piece correlated against angular position.

In the practice of this aspect of the invention, the unbalance is measured with a hard bearing measuring system that can be defined as a system where the suspension system resonance is greater than two times the running speed. As such, the workpiece is restricted from moving and the force created by the unbalance is measured, as described.

In operation, after workpiece 11 is clamped onto the precision spindle, servo motor 20 spins the workpiece at a constant measuring speed. The unbalance in the workpiece creates forces that are countered through force measuring system 40 and the force blocks (not shown) therein. The force, which is applied across piezoelectric crystals (not shown) in the force blocks generates a signal, illustratively in the form of a sine wave (not shown), corresponding to the charge signal. The charge signal is conditioned with a charge amplifier and filter 31 and then sampled by data acquisition circuit 32. In a practical embodiment of the invention, between 10 and 30 revolutions of data are sampled and synchronized by the spindle encoder. CPU processor 25 determines the unbalance amounts and corresponding angles, illustratively using synchronistic demodulation software and low pass filtering. The resulting data can be viewed by an operator (not shown) on a monitor 50, and stored on a hard disk drive 51, a conventional floppy drive 52, or any other appropriate data storage arrangement.

As previously noted, workpiece processing system 10 generates information responsive to the dimensional gaging of the workpiece. The dimensional gaging measures, in this embodiment, flatness, thickness variation, run-out, and size. These parameters are determined by measurements performed using a plurality of linear voltage differential transformer (LVDT) probes. In this embodiment, three LVDT probes 60 are evenly spaced radially along one (bottom) surface of workpiece 11, and a further three LVDT probes 61 are evenly spaced radially on an opposing (upper) surface of the workpiece. In this embodiment, each of LVDT probes 60 is arranged at a corresponding radius of the workpiece, and LVDT probes 61 are correspondingly situated.

LVDT probes 61 are shown to be vertically displaceable by operation of an air-driven slide 63. The air-driven slide withdraws a frame 64 on which LVDT probes 61 are installed away from workpiece 11. This facilitates installation of the workpiece on the precision spindle. Once the workpiece is in place, air-driven slide 63 urges frame 64 downward until a protuberance 65 on frame 66 engages with an aperture 67 in frame 64. Upon the mating of protuberance 65 with aperture 67, frames 64 and 66 are in fixed relation to one another, as are LVDT probes 60 and 61. In this specific illustrative embodiment of the invention, protuberance 65 has a generally conical configuration, and aperture 67 is correspondingly configured. However, other appropriate configurations can be provided for the protuberance and aperture, such as a spheroid, will function to effect adequate registration between frames 64 and 66.

LVDT probes 60 and 61 are commercially available and will, in this specific illustrative embodiment of the invention, communicate directly with the respective surfaces of workpiece 11. Each LVDT probe has a core (not shown) that moves linearly within primary and secondary windings (not shown) to produce a signal responsive to the location of the core. The core, of course, will be moved in response to variations in thickness or dimensional irregularities of the workpiece. The signals from the LVDT probes are conducted to a multichannel LVDT gage amplifier and filter 70 that is coupled at its output to a data acquisition circuit 71. The corresponding data is conducted to processor 25 via bus system 26.

In this specific illustrative embodiment of the invention, the measurement signals generated by LVDT probes 60 and 61 are compared with previously stored readings of a nominal size master rotor (not shown) which is used to determine whether the measurement derived from workpiece 11 under test is within predetermined tolerance. A measurement cycle would entail the placement of workpiece 11 on the measuring spindle tooling, specifically rest ring 12 which is a precision square-up ring. Collet actuator 13 is, in this embodiment, an air release collet that will spring actuate and both center and pull down the workpiece, thus gripping the workpiece so that its center line coincides with a spindle center line. In this embodiment, each of LVDTs 60 is of the air actuated type (commercially available). Upon actuation with air, LVDT probes 60 are brought into contact with the corresponding surface of workpiece 11. Upper LVDT probes 61 are then urged toward the workpiece by operation of air-driven slide 63, as previously described. LVDT probes 61 may be of the spring actuated commercially available type. Thus, all LVDT probes are directly in communication with the workpiece. Precision conical protuberance 65 and its associated conical aperture 67 ensure repeatable interengagement of frames 64 and 66, whereby precise measurements can be achieved by the LVDT probes. During measurement, precision spindle 16 turns and the LVDT probes sweep the two surfaces of workpiece 11. Corresponding analog signals are sampled periodically by data acquisition circuit 71, which signals are correlated to angular information from encoder 30, as previously described. One or more revolutions of the workpiece generate one set of measured data. Upon completion of the measurement, air-driven slide 63 restores LVDT probes 61 to the upward-most position, and an air actuation system (not shown) permits LVDT probes 60 to withdraw, whereupon the LVDT probes are no longer in communication with the workpiece.

As previously described, this specific embodiment of the invention additionally inspects the workpiece for porosity, cracks, and other surface defects. Such inspection also includes, in this embodiment, inspection for flaws and cracks in the corner 80 of workpiece 11.

In this embodiment, surface flaw detection is achieved by three eddy current probes 81, 82, and 83. These probes are of the type that emit a high frequency magnetic field. When they travel close to a metal surface, they determine the presence of flaws by changes in the reluctance in the path of the emitted magnetic field.

The eddy current probes are installed on a frame 85 which is displaceable laterally by a slide 87 in response to a servo motor 88, and vertically by an air-driven slide 89. The lateral displacement of frame 85 is controlled by processor 25 via a servo controller 90 and a servo amplifier 91.

Eddy cirrent probe 81, as will be described hereinbelow, sweeps the lower surface of workpiece 11. Eddy current probe 82 sweeps the upper surface of the workpiece, and eddy current probe 83 is a wedge-shaped eddy current probe that is specifically adapted to measure corner 80 of the workpiece. When it is desired to initiate the measurement procedure, frame 85 is lowered by air-driven slide 89 and driven laterally by slide 87 until it assumes the position represented in phantom and designated 85A, after the workpiece is installed on precision spindle 16.

In operation, the air actuated slide is activated whereby frame 85 and the eddy current probes thereon are brought to the workpiece sensing level of 85A. The servo-controlled slide 87 carries the eddy current probes towards the center of the workpiece until wedge shaped eddy current probe 83 is positioned properly in corner 80 of workpiece 11. Servo motor 20 spins precision spindle 16 and workpiece 11 for at least one turn. Multiple turns may be made in accordance with the invention. The resulting signal from the eddy current probes is conducted to an eddy current probe amplifier and filter 93 that is coupled at its output to a data acquisition circuit 94. The resulting data is delivered to processor 25 via bus system 26, and may be correlated with angular position data from encoder 30, as previously described. Each data point is then compared to determined bounds on amount and phase established to accept known good parts and to reject parts with defects. When the scan is completed, frame 85 is withdrawn laterally and then raised vertically, thereby permitting installation of another workpiece on to the precision spindle.

Figure 2:
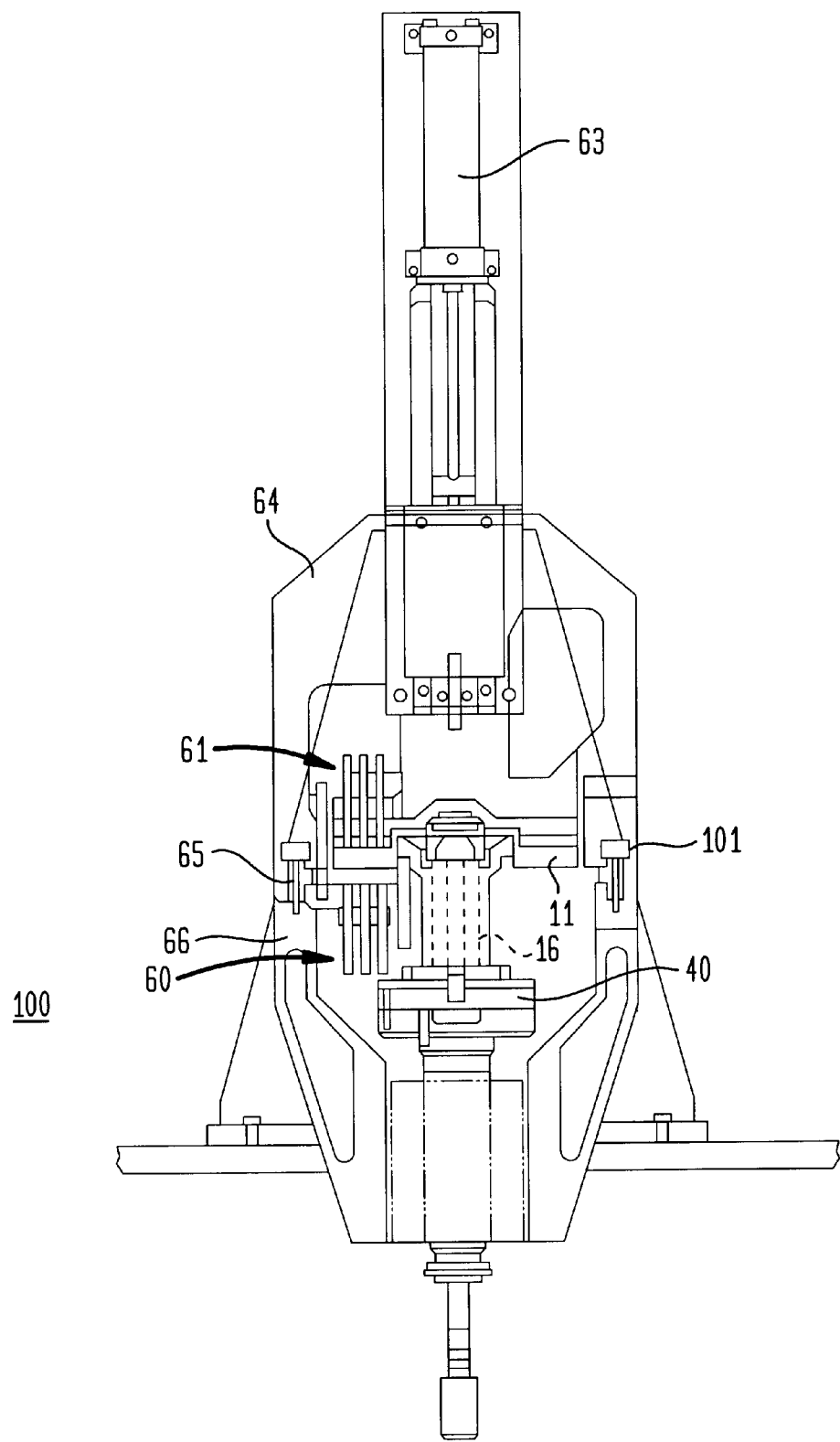
FIG. 2 is a partially phantom schematic representation that shows certain additional details of a specific illustrative embodiment of the system of FIG. 1.

FIG. 2 is a partially phantom schematic representation of a specific illustrative arrangement of the mechanical elements of a workpiece processing system 100, constructed in accordance with the principles of the invention. Elements of structure that bear analogous correspondence to those described hereinabove with respect to the embodiment of FIG. 1 are correspondingly designated.

As shown in this figure, air-driven slide 63 is coupled to frame 64 on which are disposed the three LVDT probes 61. The workpiece processing system is shown in this figure to be in a closed condition. That is, workpiece 11 is already installed on precision spindle 16, and LVDT probes 61 and 60 are directly in communication with the workpiece. Precise registration between frame 64 and frame 66 is achieved by operation of interengaging conical protuberance 65 and its associated aperture 67, as described hereinabove. However, FIG. 2 shows that there may be provided additional interengaging elements, such as interengaging element 101. Rotation of the workpiece and movement of other elements of the system preferably are performed after frame 64 has joined with frame 66, to reduce the risk of injury to the operator (not shown).

Although the invention has been described in terms of specific embodiments and applications, persons skilled in the art can, in light of this teaching, generate additional embodiments without exceeding the scope or departing from the spirit of the invention. For example, it is within the scope of the abilities of a person of ordinary skill to select appropriate LVDTs from the commercially available ones, and to select appropriate contact tips therefor. Such elements are available from the DataMyte Division of Allen-Bradley in Minetonka, Minn., and from Mitutoyo, a Japanese supplier of precision equipment. In addition, an eddy current sensing system is commercially available from SE Systems, Inc. of Hayward, Calif. Accordingly, it is to be understood that the drawing and description in this disclosure are proffered to facilitate comprehension of the invention, and should not be construed to limit the scope thereof.

What is claimed is:

1. A rotatory element processing system comprising:
    a support for supporting the rotatory element rotatably about a fixed axis of rotation;
    a drive arrangement coupled to said support for driving the rotatory element to rotate about the axis of rotation;
    a rotary encoder arrangement coupled to said drive arrangement and having an output for producing a rotation data signal containing rotational information responsive to the rotation of the rotatory element;
    an unbalance measuring arrangement for producing an unbalance data signal responsive a residual unbalance characteristic of the rotatory element;
    a surface defect detector for producing a surface defect data electrical signal responsive to a predetermined surface defect of the rotatory element;
    a first signal correlator for producing a correlated signal responsive to the rotation data signal and the unbalance data electrical signal, said signal correlator having an input for receiving the unbalance data electrical signal, and a further input for receiving the rotation data signal; and
    signal processor means for processing the surface defect data electrical signal and the correlated unbalance data signal.

2. The rotatory element processing system of claim 1, wherein there is further provided
    a further signal correlator for producing a further correlated data signal responsive to the unbalance data electrical signal, the rotation data signal, and the surface defect data signal.

3. The rotatory element processing system of claim 2, wherein there is further provided an indicator for producing an indication responsive to the further correlated data signal.

4. The rotatory element processing system of claim 1, wherein the rotatory element is of the type having first and second surfaces, and said surface defect detector comprises a first gaging probe for producing the surface data electrical signal containing data responsive to a dimensional characteristic of the first surface of the rotatory element.

5. The rotatory element processing system of claim 4, wherein there is further provided a second gaging probe for producing a further surface data electrical signal containing data responsive to a dimensional characteristic of the second surface of the rotatory element.

6. The rotatory element processing system of claim 5, wherein there is further provided a multi-channel amplifier for receiving the surface data electrical signal and the further surface data electrical signal, and for providing at an output thereof a dimensional data signal responsive to dimensional characteristics of the first and second surfaces of the rotatory element.

7. The rotatory element processing system of claim 5, wherein there is further provided a gaging probe carrier for displacing said second gaging probe from a first position in the vicinity of the second surface of the rotatory element to a second position distal from the rotatory element.

8. The rotatory element processing system of claim 7, wherein said gaging probe carrier comprises an arrangement for establishing the first position of the second gaging probe to be in fixed relation to said first gaging probe.

9. The rotatory element processing system of claim 7, wherein said gaging probe carrier further comprises a gaging probe driver for driving said second gaging probe from the first position to the second position.

10. The rotatory element processing system of claim 1, wherein there is further provided a detector carrier for displacing said surface defect detector from a first position in the vicinity of the rotatory element to a second position distal from the rotatory element.

11. The rotatory element processing system of claim 1, wherein said surface defect detector comprises an eddy current probe.

12. The rotatory element processing system of claim 10, wherein there is further provided a surface defect detector drive arrangement for driving said surface defect detector from a first position in the vicinity of the rotatory element to a second position distal from the rotatory element.

13. The rotatory element processing system of claim 12, wherein said surface defect detector drive arrangement comprises first and second drive arrangements for driving said surface defect detector along respective axes of motion.

14. The rotatory element processing system of claim 13, wherein said first and second drive arrangements comprise a servo motor drive arrangement and an air driven slide arrangement, respectively.

15. The rotatory element processing system of claim 1 wherein said unbalance measuring arrangement comprises a force measurement arrangement for producing a force signal, and wherein the unbalance data signal is responsive to the force signal.

16. The rotatory element processing system of claim 1 wherein said unbalance measuring arrangement comprises a vibration measurement arrangement for producing a vibration signal, and wherein the unbalance data signal is responsive to the vibration signal.

17. A processing arrangement for a brake element for a vehicle, the processing arrangement comprising:

a support for supporting the brake element rotatably about a fixed axis of rotation;

a drive arrangement for driving the brake element to rotate about the axis of rotation;

a rotary encoder coupled to said drive arrangement and having an output for producing a rotation data signal containing rotational information responsive to the rotation of the brake element;

an unbalance measuring arrangement for producing an unbalance data signal responsive to forces responsive to a residual unbalance characteristic of the brake element;

a surface dimension detector for producing a surface dimension data electrical signal responsive to a predetermined dimensional characteristic of the surface of the brake element;

a surface defect detector for producing a surface defect data electrical signal responsive to the presence of a predetermined surface defect of the brake element;

a signal correlator for producing a correlated signal responsive to the rotation data signal, the vibration data electrical signal, the surface dimension data signal, and the surface defect data electrical signal; and a signal processor for processing the correlated signal.

18. The processing arrangement of claim 17, wherein said support comprises a precision spindle arranged to support the brake element in a fixed axial position and rotatable about the fixed axis of rotation.

19. The processing arrangement of claim 18, wherein there is further provided a fixed support, and said vibration measuring arrangement comprises a force measuring block interposed between said precision spindle and the fixed support.

20. The processing arrangement of claim 17, wherein said surface dimension detector comprises a first linear voltage differential transformer probe arranged to communicate with a first surface of the brake element.

21. The processing arrangement of claim 20, wherein said surface dimension detector further comprises:

a second linear voltage differential transformer probe arranged to communicate with a second surface of the brake element; and a dimension detector carrier for displacing said second linear voltage differential transformer probe from a first position in the vicinity of the second surface of the brake element to a second position distal from the brake element.

22. The processing arrangement of claim 17, wherein said surface defect detector comprises an eddy current detector probe.

23. The processing arrangement of claim 17, wherein said signal processor comprises:

a data acquisition arrangement for acquiring data contained in respective ones of the rotation data signal, the vibration data electrical signal, the surface dimension data signal, and the surface defect data electrical signal;

a central processor unit for producing an output data signal responsive to the rotation data signal, the vibration data electrical signal, the surface dimension data signal, and the surface defect data electrical signal; and a bus for coupling said data acquisition arrangement to said central processor unit.

24. The processing arrangement of claim 23, wherein there are further provided:

a display coupled to said central processor unit for producing a visual indication responsive to the rotation data signal and the vibration data electrical signal; and a data storage arrangement for storing data responsive to the rotation data signal and the vibration data electrical signal.

25. A method of processing a rotatory element, the method comprising the steps of:

installing the rotatory element on a rotatable spindle having a longitudinal axis;

rotating the rotatory element and the rotatable spindle about the longitudinal axis;

producing a rotation signal responsive to the rotation of the rotatory element in said step of rotating;

producing a surface defect signal by translating an eddy current probe across a surface of the rotatory element;

producing an unbalance signal responsive to the rotation of the rotatory element in said step of rotating; and producing a dimension signal responsive to a predetermined dimension of the rotatory element in the direction of the longitudinal axis during said step of rotating.

26. The method of claim 25, wherein there is further provided the step of acquiring data responsive to the rotation signal, the unbalance signal, and dimensional signal.

27. The method of claim 26, wherein there is further provided the step of producing a visual indication responsive to the data obtained in said step of acquiring.

28. The method of claim 25, wherein, prior to performing said step of producing a dimension signal, there is further provided the step of translating a dimensional probe to a predetermined location with respect to the rotatory element.

* * * * *